(12) United States Patent
Knupfer et al.

(10) Patent No.: US 8,605,146 B2
(45) Date of Patent: Dec. 10, 2013

(54) APPARATUS FOR OPTICALLY INSPECTING AN AT LEAST PARTIALLY REFLECTING SURFACE OF AN OBJECT

(75) Inventors: Klaus-Georg Knupfer, Essingen (DE); Joachim Reimann, Bad Boll (DE); Volker Huss, Süssen (DE); Volker Schöllkopf, Bad Boll (DE)

(73) Assignee: Carl Zeiss OIM GmbH, Wangen (DE)

( * ) Notice: Subject to any disclaimer, the term of this patent is extended or adjusted under 35 U.S.C. 154(b) by 3 days.

(21) Appl. No.: 13/171,105

(22) Filed: Jun. 28, 2011

(65) Prior Publication Data

US 2011/0310242 A1 Dec. 22, 2011

Related U.S. Application Data

(63) Continuation of application No. PCT/DE2009/001812, filed on Dec. 23, 2009.

(30) Foreign Application Priority Data

Dec. 29, 2008 (DE) .......................... 10 2008 064 562

(51) Int. Cl.
 *H04N 7/18* (2006.01)
(52) U.S. Cl.
 USPC ..... 348/92; 356/237.1; 356/237.2; 356/237.3
(58) Field of Classification Search
 USPC .............. 348/92, 131; 356/237.1–237.6, 613; 362/253, 373; 414/239; 315/291
 See application file for complete search history.

(56) References Cited

U.S. PATENT DOCUMENTS

| | | | |
|---|---|---|---|
| 4,918,321 A | | 4/1990 | Klenk et al. |
| 5,060,065 A | * | 10/1991 | Wasserman .................... 348/131 |

(Continued)

FOREIGN PATENT DOCUMENTS

| | | |
|---|---|---|
| DE | 198 21 059 A1 | 12/1999 |
| DE | 101 29 972 A1 | 1/2003 |
| DE | 103 17 078 A1 | 10/2004 |
| DE | 20 2004 009 194 U1 | 12/2004 |
| DE | 10 2005 038 535 A1 | 2/2007 |
| DE | 10 2007 063 530 A1 | 7/2009 |
| JP | 2000031546 A | 1/2000 |
| WO | 2009007130 A1 | 1/2009 |

OTHER PUBLICATIONS

International Search Report dated May 27, 2010 of international application PCT/DE 2009/001812 on which this application is based.
Kammel, S., "Deflectometry for Quality Control of Specular Surfaces", tm—Technisches Messen 70 (2003)4, pp. 193 to 198, Oldenbourg Verlag.

*Primary Examiner* — Sath V Perungavoor
*Assistant Examiner* — Nathnael Aynalem
(74) *Attorney, Agent, or Firm* — Walter Ottesen P.A.

(57) ABSTRACT

An apparatus for optically inspecting an at least partially reflecting surface of an object includes first and second transverse carriers (12, 14) defining respective substantially circular segment-shaped cutouts (32). The transverse carriers (12, 14) are disposed at a longitudinal distance (D) from one another and the longitudinal distance (D) defines a longitudinal direction (17). A plurality of longitudinal members are configured to hold the first and second transverse carriers at the longitudinal distance (D). The longitudinal members are arranged at a defined radial distance to the circular segment-shaped cutouts. A translucent diffusing screen is held in the circular segment-shaped cutouts by the transverse carriers to form a tunnel-shaped inspection space. A multiplicity of light sources are arranged outside of the tunnel-shaped inspection space behind the diffusing screen. The light sources are configured to be controlled individually or in small groups to generate variable light-dark patterns on the diffusing screen. A workpiece receptacle is configured for accommodating the object in the tunnel-shaped inspection space. At least one camera is directed into the tunnel-shaped inspection space. An evaluation and control unit is configured to control the light sources and the camera to generate various light-dark patterns on the diffusing screen and to record and evaluate a plurality of images of the object in dependence on the light-dark patterns.

16 Claims, 5 Drawing Sheets

(56) References Cited

U.S. PATENT DOCUMENTS

| | | | |
|---|---|---|---|
| 5,636,024 A * | 6/1997 | Crookham et al. | 356/613 |
| 5,726,705 A * | 3/1998 | Imanishi et al. | 348/92 |
| 5,726,706 A | 3/1998 | Walsh | |
| 6,100,990 A | 8/2000 | Ladewski | |
| 7,599,050 B2 | 10/2009 | Ishikawa et al. | |
| 2003/0119990 A1 * | 6/2003 | Bruneau et al. | 525/199 |
| 2005/0040772 A1 * | 2/2005 | Guzman et al. | 315/291 |
| 2007/0047239 A1 * | 3/2007 | Kang et al. | 362/373 |
| 2007/0097686 A1 * | 5/2007 | Dunn et al. | 362/252 |
| 2009/0016863 A1 * | 1/2009 | Rauch et al. | 414/239 |

* cited by examiner

APPARATUS FOR OPTICALLY INSPECTING AN AT LEAST PARTIALLY REFLECTING SURFACE OF AN OBJECT

CROSS REFERENCE TO RELATED APPLICATIONS

This application is a continuation application of international patent application PCT/DE 2009/001812, filed Dec. 23, 2009, designating the United States and claiming priority from German application 10 2008 064 562.1, filed Dec. 29, 2008, and the entire content of both applications is incorporated herein by reference.

FIELD OF THE INVENTION

The invention relates to an apparatus for optically inspecting an at least partially reflecting surface of an object. In particular, the invention relates to an apparatus which enables a largely automatic or even fully automatic inspection of a reflecting surface under industrial conditions.

BACKGROUND OF THE INVENTION

In industrial manufacturing of products, for many years now, the product quality has played an increasingly important role. On the one hand, high product quality can be achieved by correspondingly designed and stable manufacturing processes. On the other hand, the quality parameters of a product must be inspected in a manner as reliable and complete as possible in order to detect quality deficiencies at an early stage. In many cases, the quality of a product surface plays a role. This may involve decorative surfaces such as painted surfaces on automobiles or household items, or technical surfaces such as surfaces of finely worked metallic pistons or bearing surfaces.

There are already many suggestions and concepts for automatically inspecting reflecting surfaces. Often, however, the known methods and apparatus can only be used for a specific application because they require a high a priori knowledge of the surface to be inspected. Furthermore, the known methods and apparatus are not sufficiently perfected to enable an efficient and reliable inspection of surfaces under industrial conditions. In this case, industrial conditions refer to the compliance with cycle times, which are relevant for inclusion in industrial manufacture, the ability to perform the surface inspection in a manufacturing hall, and/or the possibility to simply and quickly adapt the surface inspection to changing products.

Consequently, for example, in the automobile industry, up until today, a visual inspection of paint surfaces is performed to a significant degree by experienced and trained persons. The degree of automation in the inspection of reflective painted surfaces is substantially lower than the degree of automation in the manufacture itself. An example of an apparatus for the visual inspection of the painted surface of a motor vehicle is described in U.S. Pat. No. 5,636,024. The apparatus includes a tunnel through which the motor vehicles with the painted surfaces to be inspected are transported. There are light sources on the inner walls of the tunnel which generate a striped pattern of light and dark stripes. These striped patterns are reflected by the painted surface of the motor vehicle. The inspection of the painted surface is carried out by persons who are standing in the tunnel and are visually checking the reflections of the striped pattern on the painted surface. It is easily comprehensible that such a procedure to a large extent depends on the skills of the observer and thus provides limited reliability only. Furthermore, such a procedure is work intensive and accordingly expensive.

German patent publication 103 17 078 A1 describes a deflectometric method and a corresponding apparatus. In this method, a striped pattern with a sinusoidal brightness gradient is projected onto a screen which is arranged obliquely to the surface to be inspected. The projected pattern is changed or moved so that correspondingly changed striped patterns hit the surface. While or after the changing/moving of the pattern an image of the surface with the reflected pattern is recorded. Through a mathematical linking of the images taken at different points in time, a result image is to be generated on the basis of which areas of the surface having defects and areas of the surface devoid of defects can be mathematically or visually differentiated. A similar method and a similar apparatus are known from a publication by Sören Kammel entitled: "Deflectometry for the Quality Testing of Specularly Reflecting Surfaces", published in the German magazine tm-technisches Messen, edition April, 2003, pages 193 to 198. In this case, an evaluation of the obtained image data is carried out by comparison to a reference, which requires an exact alignment of the surface to be examined to the reference data.

Further methods and apparatus for the optical inspection of at least partially reflecting surfaces are disclosed in German patent publication 198 21 059 C2 or in U.S. Pat. 6,100,990. Here too, striped patterns with sinusoidal brightness gradient across the surface to be inspected are observed. In all cases, the striped patterns are created on a screen which is arranged at an angle to the surface to be inspected. These methods thus have the disadvantage that only a relatively small surface can be inspected, which in addition must be arranged in an at least mostly known and defined position and alignment to the striped pattern. A quick, reliable and efficient inspection of reflecting surfaces under industrial conditions is not possible therewith.

U.S. Pat. Nos. 5,726,706 and 4,918,321 each disclose a method and apparatus wherein a motor vehicle is passed under a bridge-like arrangement on which a plurality of cameras are arranged. The detection of paint defects or other surface defects is done with the aid of light stripes or light bands whose reflection is analyzed. In a defect-free surface, each camera sees the respective light or dark stripes. A surface defect, such as a dent, results in the light to be diverted from a light stripe into the image of a dark stripe so that a bright light point is visible in the image of the dark stripe. These methods have limited detection rates. Small scratches or duller paint areas which do not create any considerable reflections in any other direction in space but the surrounding areas cannot be detected with these apparatus.

German patent publication 10 2005 038 535 A1 recognized the problems encountered with the adaptation of the surface inspection to the cycle times of industrial manufacturing and suggests a rotation-symmetrical, in particular cylindrical stripe projector for illuminating an object having a surface to be inspected. A cylindrical hollow body has its inner wall provided or coated with an electroluminescent foil. The foil is to be provided with colored or gray-scale stripes which are either printed thereon or realized with the help of a second foil. The cylindrical hollow body is to be mounted in a second, outer hollow body in such a manner that it can be mechanically put into a rotational movement. The rotational movement is to generate the change in the striped pattern relative to the surface to be inspected. The mechanical movement of the cylindrical hollow body, however, constitutes a disadvantage of this concept, in particular, if the apparatus is to be used for the inspection of objects with large surfaces.

SUMMARY OF THE INVENTION

It is an object of the invention to provide an apparatus which enables a quick and at least largely automated inspection of objects having reflective surfaces under industrial conditions. Accordingly, it is desirable that the apparatus can be realized in a manner as cost efficient and subject to as little wear as possible and in principal facilitates the inspection of very large and very small objects.

The apparatus of the invention is for optically inspecting an at least partially reflecting surface of an object. The apparatus includes: first and second transverse carriers defining respective substantially circular segment-shaped cutouts; the first and second transverse carriers being arranged at a longitudinal distance (D) from each other and the longitudinal distance defining a longitudinal direction; a plurality of longitudinal members configured to hold the first and second transverse carriers at the longitudinal distance (D); the longitudinal members being arranged at a defined radial distance to the circular segment-shaped cutouts; a translucent diffusing screen which is held in the circular segment-shaped cutouts by the transverse carriers to form a tunnel-shaped inspection space; a multiplicity of light sources arranged outside of the tunnel-shaped inspection space behind the diffusing screen; the light sources being configured to be controlled individually or in small groups to generate variable light-dark patterns on the diffusing screen; a workpiece receptacle configured for accommodating the object in the tunnel-shaped inspection space; at least one camera which is directed into the tunnel-shaped inspection space; and, an evaluation and control unit configured to control the light sources and the camera to generate different ones of the light-dark patterns on the diffusing screen and to record and evaluate a plurality of images of the object in dependence on the light-dark patterns.

The new apparatus uses a tunnel-shaped inspection space in which the object having the surface to be inspected is introduced. The tunnel-shaped inspection space surrounds the object over an arc length of at least 90°, preferably over an arc length of more than 120° and in particularly preferred embodiments with an arc length of approximately 180° or more. Consequently, the light-dark patterns generated on the diffusing screen hit the surface to be inspected from multiple directions, a circumstance which makes the inspection of objects with complex free-form surfaces easier and faster. It is sufficient if the object to be inspected is arranged in the tunnel-shaped inspection space. A specific and/or exact positioning of the object in the inspection space may generally be omitted, unless the object has dirty surfaces and/or undercuts which must be arranged in such a manner that they are facing at least the one camera.

The multiplicity of light sources, which can be controlled individually or in small groups, makes it possible to generate a plurality of different light-dark patterns. Thus, this new apparatus can very easily and quickly be adapted to different requirements. Moreover, a mechanical motion of the tunnel can be omitted, a fact which is especially advantageous in the inspection of large objects such as motor vehicles or motor vehicle parts. Since the plurality of individually controllable light sources also enables shifting or moving of a defined light-dark pattern relative to the object, the workpiece receptacle can be stationary in principle. In some embodiments, the floor of a factory or the like can be the workpiece receptacle. The latter is advantageous if the objects to be inspected are self-propelled and/or are transportable into the tunnel-shaped inspection space on a pallet or a transport cart.

The arrangement with the at least two transverse carriers and the longitudinal members enables a modular and scalable configuration and consequently a cost-effective realization.

The evaluation and control unit in preferred embodiments is configured to control the light sources and the camera so that the surface to be inspected is recorded in at least four different positions relative to a defined light-dark pattern.

That is to say, at least four images of the object to be inspected are available, in which there is a defined light-dark pattern in four different positions relative to the surface. The light-dark pattern in this case preferably has a sinusoidal brightness gradient. The evaluation and control unit is advantageously configured to determine the phase position of the brightness gradient relative to the surface to be inspected on the basis of the images, since the phase position correlates to a local inclination of the surface. On the basis of the local inclination various surface defects on reflecting surfaces can be detected with a high degree of precision and reliability.

Overall, the new apparatus is based on a concept which basically enables an automated and thus fast and reliable surface inspection on different and differently sized objects. Because of the modular and largely scalable concept, the new apparatus can be realized for a variety of applications in a cost-effective manner. The apparatus can be easily and quickly adapted to changing inspection tasks because of the individually controllable light sources. Because of the tunnel-shaped inspection space which forms a defined and outwardly delimited inspection volume the apparatus can be used in quite a problem-free manner under real manufacturing conditions, a fact which enables a quality inspection close to the location of manufacture.

In a preferred embodiment of the invention, the new apparatus has a plurality of identical light modules which are arranged between the diffusing screen and the longitudinal members. Each light module includes a plurality of light sources. It is especially advantageous if the identical light modules each have a front side which is completely covered with light sources.

The arrangement of the light modules between the diffusing screen and the longitudinal members enables undisturbed, shadow-free generation of the light-dark patterns on the diffusing screen. This is advantageous to generate largely any light-dark patterns and to let them "wander" over the diffusing screen. For the same reason, it is advantageous when the front sides of the light modules are completely covered with light sources and together form a largely homogenous area on which the light sources are arranged in rows and columns relative to each other at regular lateral distances. The use of identical light modules reduces the production and maintenance costs.

In a further embodiment, the light modules have a metallic carrier body having a length which is about equal to the defined longitudinal distance. The carrier body has a front side on which the light sources are arranged, as well as a back side on which cooling fins are formed. The light sources are preferably arranged on a thin, flexible carrier foil, which is not very rigid, and is adhesively bonded directly on the front side of the cooling body.

In this embodiment, the light modules have a metallic, preferably rigid and thus self-supporting carrier body which has a good thermal conductivity. Cooling fins are, preferably integrally, formed on the back side of the carrier body and preferably extend in the longitudinal direction. The result of the latter is that the cooling fins of all light modules point radially outwardly. The plurality of light modules thus form an integrated cooling body which promotes a heat transfer and a defined air flow over the light modules. The arrangement of the light sources on a thin carrier foil and the direct adhesive bonding of this foil on the cooling body also contribute to the good heat transfer in a very advantageous manner. In a particularly preferred variant of this embodiment, a conducting plate, which includes the control and driver circuits for controlling the light sources, is arranged directly on one of the cooling fins. In addition, it is preferred that the carrier foil with the light sources has integral (connected as one piece to the carrier foil) straps on at least one side. The straps are bent around the cooling body and connected to the conducting plate. These variants enable a very compact electrical connection of the light sources to the control electronics. Further, the light sources can be easily mounted and a maximum thermal coupling of the light sources on the cooling body is achieved.

These configurations are very advantageous alone and in combination for the accommodation of a desired large amount of separate, individually controllable light sources with small lateral distances and for a stable operation of the same. As has been shown in practical experiments, it is difficult to integrate an efficient cooling for many light sources in a compact design optimized for flexible pattern generation. The embodiments described herein have proven to be very advantageous is this respect because they promote a direct heat transfer radially outwardly and in the longitudinal direction.

In a further embodiment, the light modules are mounted floatingly on the transverse carriers floating in the longitudinal direction. In one embodiment, the light modules are each mounted via a fixed support at a first end and via a floating support at an opposing second end.

In this embodiment, the at least two transverse carriers are held at the defined longitudinal distance essentially or even completely with the help of longitudinal carriers. As a matter of fact, the light modules extend from one transverse carrier to the other. However, they are exempt from mechanically fixing the transverse carriers at the longitudinal distance. A floating mounting of the light modules with a spring-loaded floating support enables a defined alignment of the light sources in a simple and cost efficient manner but allows for an expansion of the light modules in the longitudinal direction. This expansion is favored if the length of the individual light modules is substantially larger than their widths. In a preferred embodiment, the length of the light modules in the longitudinal direction is larger than the width by a factor of 10 or more, measured on the front sides of the light modules, on which sides the light sources are arranged. Such proportions of the light modules favor a thermally conditioned expansion in the longitudinal direction which can be compensated for via a spring-loaded floating support in a more or less tension-free manner. Surprisingly, a movable mounting of the light sources is acceptable, even though the patterns on the diffusing screen can change as a result. The configurations also advantageously contribute to reduce the thermally conditioned tensions inside the new apparatus.

In a further embodiment, each light module has two rows of light sources in parallel in the longitudinal direction, and the light sources can be separately controlled.

In principle, each light module could only have one row of light sources or more than two rows of light sources on its front side with the light sources being independently controllable. Two rows, however, are advantageous because, on the one hand, they provide a higher integration density in comparison to light modules having only one row of the light sources. On the other hand, two parallel rows have the advantage that circles with almost any radius can be defined transversely to the parallel rows. This enables the positioning of all separately controllable light sources at an optimal radial distance to the diffusing screen, that is, largely independent of the actual inner radius of the diffusing screen. For this reason, this configuration is especially advantageous for the scaling of the new apparatus. Irrespective of the chosen size of the inner radius of the tunnel-shaped inspection space, the light modules can always be positioned at an optimal distance to the diffusing screen because of this configuration:

In a further embodiment, the light sources are arranged with the same equal radial distances to the diffusing screen.

This ensures a consistently high detail and precision of the light-dark patterns.

In an especially preferred embodiment, each light module has four rows of light sources on its front side. Four light sources from two neighboring rows, which form a square 4-tuple, are controlled together. Each 4-tuple forms a virtual light source having four times the light output of a single light source.

This embodiment enables a very cost-effective realization of universally usable light modules and thus contributes to an especially cost-effective realization of the new apparatus.

In a further embodiment the diffusing screen is a milkglass-like ground glass.

In this embodiment, the diffusing screen is a translucent but non-transparent and preferably diffusely scattering ground glass. In an embodiment, the ground glass can be a flexible plastic plate, in particular of acrylic glass (PMMA) or a full-volume PTFE material. A milkglass-like ground glass "mixes" the luminous radiation of adjacent light sources because of its scatter characteristics. This is a fact which is advantageous for the generation of light-dark patterns with smooth light-dark transitions. As has been shown in studies conducted by the applicants, light-dark patterns of this kind are particularly suited for a comprehensive inspection of reflecting surfaces.

In a further embodiment, the diffusing screen is floatingly mounted on the transverse carriers.

In this embodiment, only the radius of the diffusing screen is fixed by the transverse carriers. Further, the diffusing screen can move in the longitudinal direction and/or tangentially to the longitudinal direction. This configuration is very advantageous for reducing the thermal tension in the apparatus.

Furthermore, it has been shown that a floating mounting of the diffusing screen in the longitudinal and/or tangential direction does not have a noticeably negative effect on the reliability and detection reliability when inspecting reflecting surfaces. Irrespective thereof, embodiments of the new apparatus can include that the diffusing screen is coupled with a position detector which detects a size- and/or position change of the diffusing screen. Such a position detector can, for example, be realized with the aid of reference markings which are arranged on the diffusing screen. With such embodiments, a temperature compensation can be realized which compensates a thermally conditioned change in the light-dark pattern. The embodiments preferred at this time, however, do not require temperature compensation, especially when the radius of the diffusing screen is fixed by the transverse carriers.

In a further embodiment, the transverse carriers have holding clamps which are configured to replaceably fix the diffusing screen. In some embodiments, the diffusing screen is a flexible plate which is held at a defined radius with the aid of the transverse carriers. In other embodiments, the diffusing screen is bent in advance by an amount required. Advantageously, the circular segment-shaped sections of the at least two transverse carriers align with each other, which fact facilitates a simple insertion of the diffusing screen in the sections. Further, it is preferred that the diffusing screen can integrally be inserted into the largely circular segment-shaped sections when the transverse carriers and holding clamps are configured in such a manner.

In the new apparatus, the tunnel-shaped inspection space is largely delimited by the translucent diffusing screen. For this reason, the diffusing screen is susceptible to soiling which can be avoided only with difficulty in a manufacturing environment. The soiling of the diffusing screen also influences the quality of the light-dark patterns. For this reason, it is advantageous if the diffusing screen can be easily and quickly replaced, a fact which the present embodiment accomplishes in a convenient manner.

In a further embodiment, the apparatus has a plurality of fans which are arranged on the longitudinal members. Each longitudinal member preferably has at least one fan which generates a defined air flow radially inwardly.

This configuration is advantageous because the fans thermally stabilize the longitudinal members. Because the longitudinal members also serve to hold the transverse carriers at a defined longitudinal distance, this configuration advantageously contributes to the reduction of thermally induced tensions. This configuration is especially advantageous in combination with a floatingly mounted diffusing screen and/or floatingly mounted light modules, because the stability is ensured in the longitudinal direction, in particular because of the directly cooled longitudinal members. The fans advantageously draw in fresh cooling air from outside and blow it outward over the light modules. The fresh cooling air is preferably drawn in via air filters in order to avoid blowing dust particles into the apparatus. Alternatively, the fans could draw in cooling air over the light modules and blow the warm exhaust air toward the outside. The drawing-in and blowing-in of the fresh cooling air, however, is preferred because it has the positive side effect of generating a constant cleaning of the apparatus by means of the dirt particles present in the apparatus being blown out.

In a further embodiment, the longitudinal members form a largely closed cover which is arranged approximately concentrically to the diffusing screen.

This embodiment is also very advantageous to enable a thermally stable and largely tension-free construction of the new apparatus. The longitudinal members form a closed cover which enables a defined and flow-optimized cooling air flow past the hot light sources.

In a further embodiment, the transverse carriers are arranged vertically over each other.

In this configuration, the new apparatus includes a "standing tunnel" or a tunnel-like column which forms the inspection space. The introduction of objects into the inspection space can advantageously be effected from below or through an entrance on the side. Alternatively, the new apparatus can be realized with a "lying" tunnel and also with a tunnel which is open on the side in the longitudinal direction. The latter is advantageous when the test item and/or the at least one camera are arranged on a robotic arm which can move along the open longitudinal side of the tunnel. A standing tunnel in comparison enables a very compact apparatus with a small "footprint". Further, a standing tunnel is also advantageous for efficient cooling, especially when the individual light modules have cooling fins extending in the longitudinal direction, because in this case a chimney effect sets in.

In a further embodiment, the apparatus has a transverse beam on which the at least one camera is arranged. The transverse beam is arranged outside of the tunnel-shaped inspection space in the longitudinal direction. In preferred variants, the transverse beam is fixed on one of the transverse carriers. Advantageously, the transverse carrier has a plurality of prepared mounting positions on which the transverse beam can be fixed. This configuration, on the one hand, enables a variable angle of view for the camera in the tunnel-shaped inspection space. On the other hand, it enables a simple exchange of the diffusing screen in the longitudinal direction.

In a further embodiment, the at least one camera has an optical axis which is arranged largely perpendicular to the longitudinal direction. In an embodiment, the apparatus has a plurality of cameras, one of which looks into the inspection space perpendicularly to the longitudinal direction. This camera can advantageously be a line-scan camera if the workpiece receptacle enables a rotational movement of the object about an axis in parallel to the longitudinal direction. The latter is especially preferred if the line-scan camera looks into the inspection space through a narrow slit between the light sources.

These embodiments enable a very fast and flexible receiving of images of the surface to be inspected with a light-dark pattern.

In a further embodiment, the apparatus includes at least one closing plate which closes the tunnel-shaped inspection space in the longitudinal direction. The closing plate has an inner side directed into the inspection space, which side is configured so as to generate a further pattern with light and dark regions. The inner side of the closing plate can be provided with mirrors which reflect a light-dark pattern generated with the help of the light sources onto the surface to be inspected. Alternatively or additionally thereto, the inner side can be equipped with further light sources which can be controlled individually or in small groups. In principle, the inner side can also have a defined light-dark pattern printed thereon which is illuminated with the help of the existing light sources. These configurations are advantageous to enable an inspection of surfaces which are arranged largely transverse or nearly in parallel to the longitudinal direction of the inspection space. The closing plate therefore simplifies a fast and comprehensive inspection of objects of any shape.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
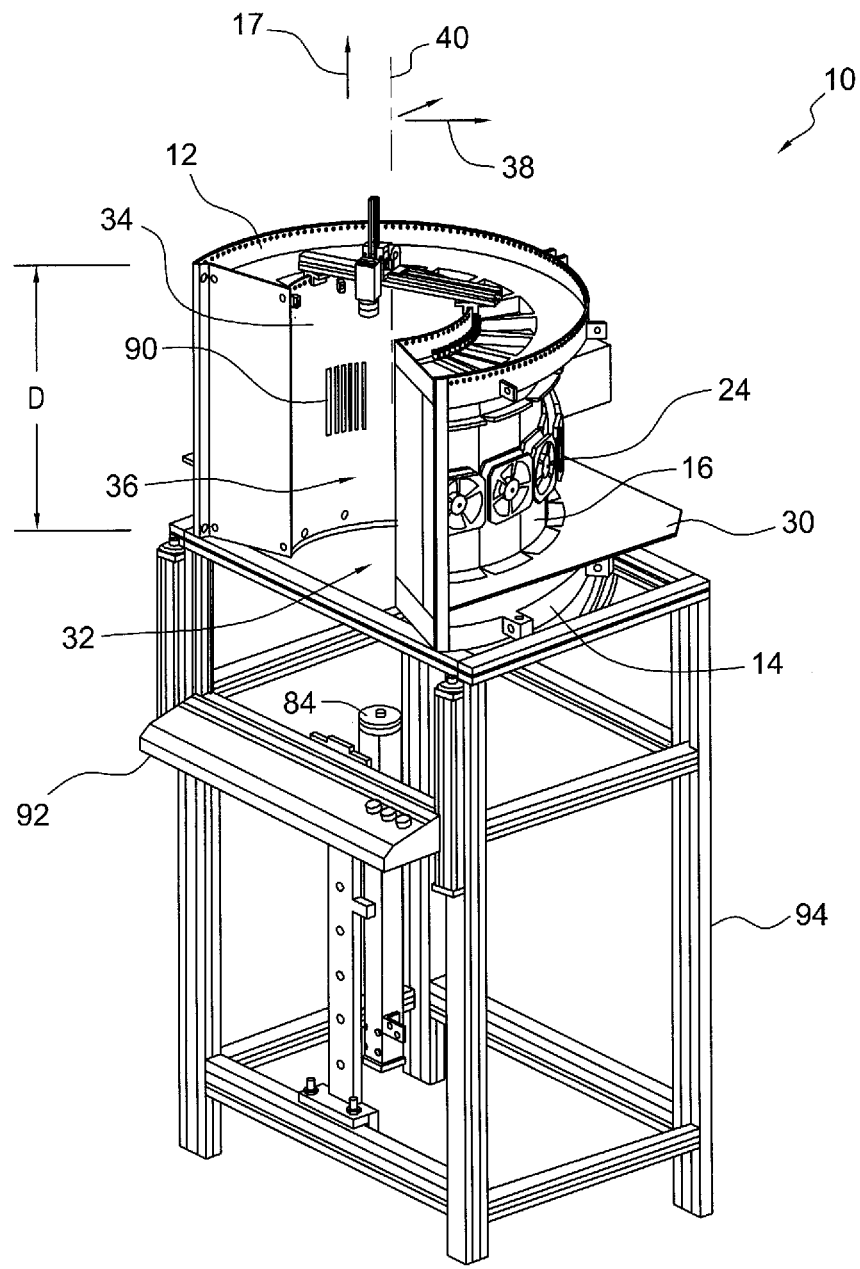
FIG. 1 shows a perspective view of a preferred embodiment of the new apparatus.
Figure 2:
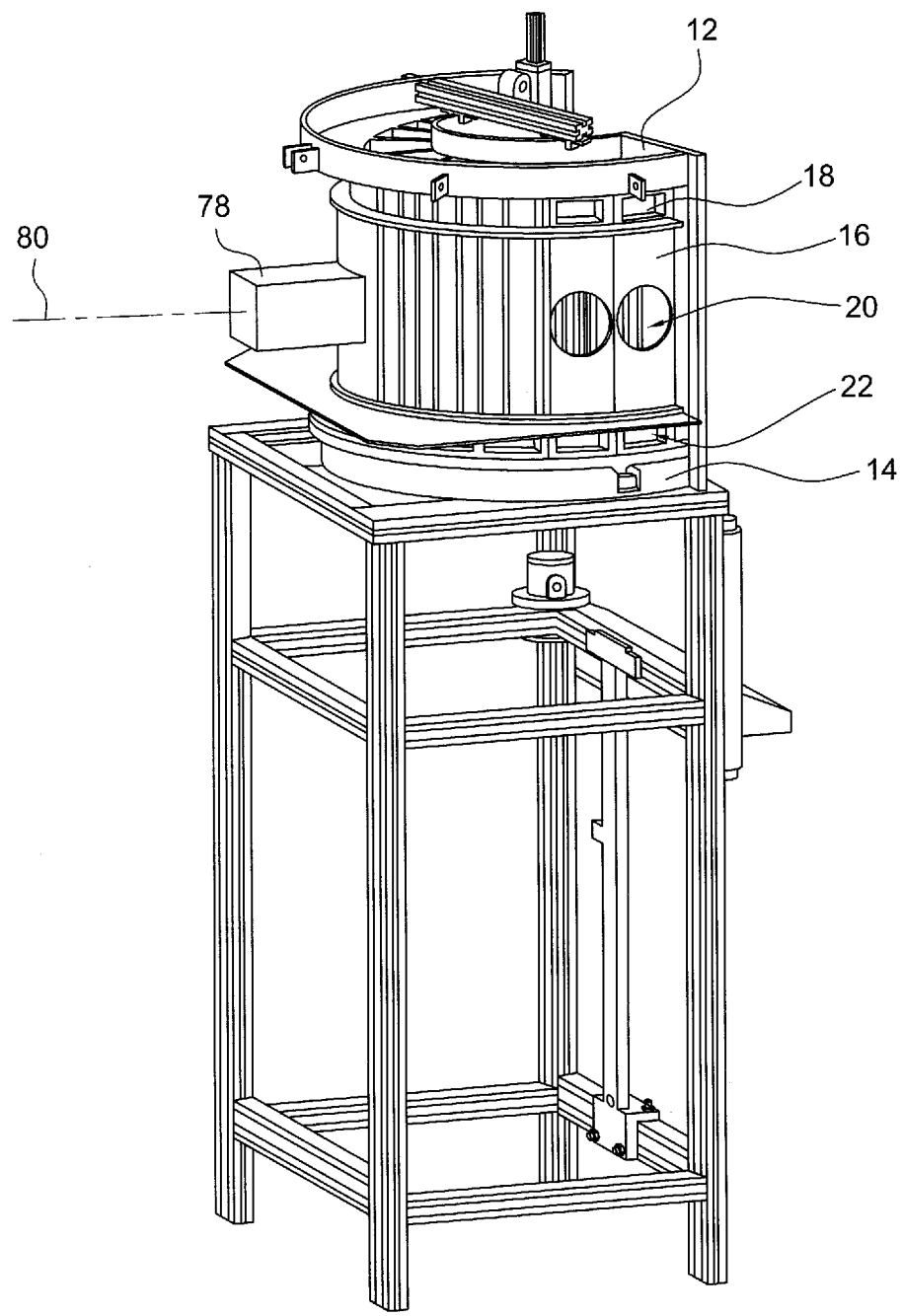
FIG. 2 shows the apparatus of FIG. 1 in a view from behind at an angle, whereby several parts are omitted for the sake of clarity.
Figure 3:
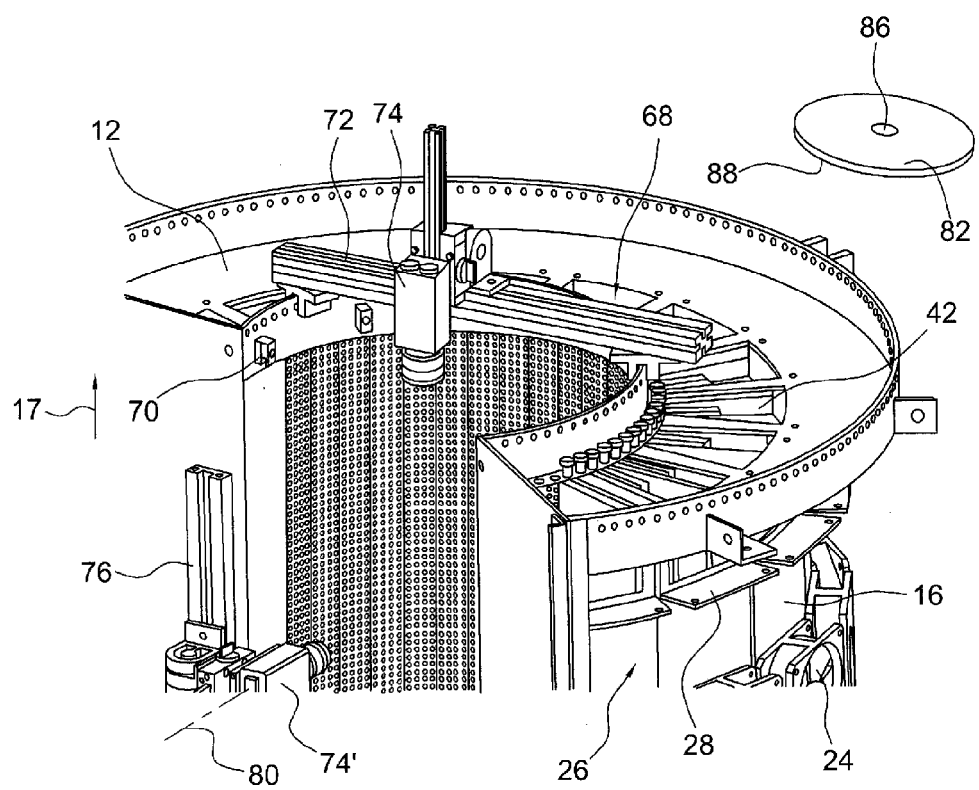
FIG. 3 shows an enlarged detail view of the apparatus of FIGS. 1 and 2.

FIGS. 1 to 3 show a preferred embodiment of the new apparatus in its entirety referenced with the reference number 10. The apparatus 10 here is realized in the form of a "standing tunnel", that is in the form of a column with a vertical, tunnel-shaped inspection space. Deviating therefrom, the apparatus 10 can be realized in other embodiments with a "lying tunnel", that is, with an inspection space extending in the horizontal direction. It is also conceivable to realize the tunnel-shaped inspection space with the help of two or more tong-like or plier-like parts which can be opened or closed. Such an embodiment is especially advantageous if the tunnel-shaped inspection space is to be closed from all sides. In the embodiment shown in FIGS. 1 to 3, the "vertical tunnel", however, is open at the top and bottom ends. Further, the apparatus 10 has a lateral access into the inspection space.

The apparatus 10 has a top transverse carrier 12 and a bottom transverse carrier 14. Here, the transverse carriers (12, 14) are C-shaped with an arc length of a little more than 180°. The transverse carriers (12, 14) are held at a defined longitudinal distance D, which defines a longitudinal direction 17, by a plurality of longitudinal carriers 16.

In the embodiment shown, the longitudinal carriers 16 are rectangular metal plates. The plurality of metal plates have a top opening 18, a middle opening 20 and a bottom opening 22. Here, the middle opening 20 is circular and serves for mounting a fan 24. The top opening 18 and the bottom opening 22, here, are approximately rectangular. The fans 24 draw in cool fresh air from outside (preferably through an air filter, not shown here, which is mounted above the fan 24) and blow it as cooling air through the middle opening 20 and into the apparatus 10. The openings (18, 22) serve as outlet openings via which the warm exhaust air gets back to outside. The fans 24, thereby, generate a defined air flow which enables an efficient cooling of the light sources described hereinafter. The efficient cooling, here, is supported by the plate-shaped configuration of the longitudinal carriers 16, since the closed plate regions of the longitudinal carriers 16 form a largely closed enclosure 26, which is arranged approximately concentrically to the tunnel-shaped inspection space (FIG. 3).

According to a particularly preferred embodiment each longitudinal carrier 16 has a mounting bracket 28 below the top opening 18 and above the bottom opening 22. In the preferred embodiments, an upper (not shown here) and a lower air baffle 30 are arranged on the mounting brackets 28, which separate the cool supply air and the heated exhaust air from one another. The longitudinal carriers 16 fulfill an advantageous dual function here. On the one hand, they are mechanically connected to the transverse carriers (12, 14) in order to fixedly hold the transverse carriers (12, 14) at a defined distance D. The transverse carries (12, 14) and the longitudinal carriers 16 can be welded together or, as is the case here, connected to each other via threaded fasteners. Furthermore, the plate-shaped longitudinal carriers 16 delimit the flow channel for the cooling air and exhaust air.

The transverse carriers (12, 14) each have a largely circular segment-shaped cutout 32. In a preferred embodiment the C-shaped transverse carriers (12, 14) are configured exactly circular shaped, that is they represent a segment of a circular ring. Accordingly, the outer peripheries of the transverse carriers (12, 14) are concentric, here, to the circular segment-shaped cutout 32. Circular segment-shaped cutouts 32 are advantageous in order to hold the translucent diffusing screen, identified by reference character 34, in a defined alignment. The diffusing screen 34 forms the tunnel-shaped inspection space 36. Principally, however, it is conceivable to realize the tunnel-shaped inspection space 36 with a cross-section which deviates from an exact circular shape or from a circular segment. The inspection space 36 could, for example, have a polygonal cross-section or an elliptical cross-section.

As one can see in FIG. 1, the plate-shaped longitudinal carriers 16 are arranged largely concentrically to the tunnel-shaped inspection space 36 in the shown embodiment. In other words, the longitudinal carriers 16 are arranged in a defined radial distance to the circular segment-shaped cutouts 32. The radial distance in FIG. 1 is indicated by reference character 38. The radial distance, here, relates to the longitudinal center axis 40 which intersects the circular segment-shaped cutout 32 at its center point. In the shown embodiment, the circular segment-shaped cutouts 32 align along the longitudinal center axis 40.

Figure 4:
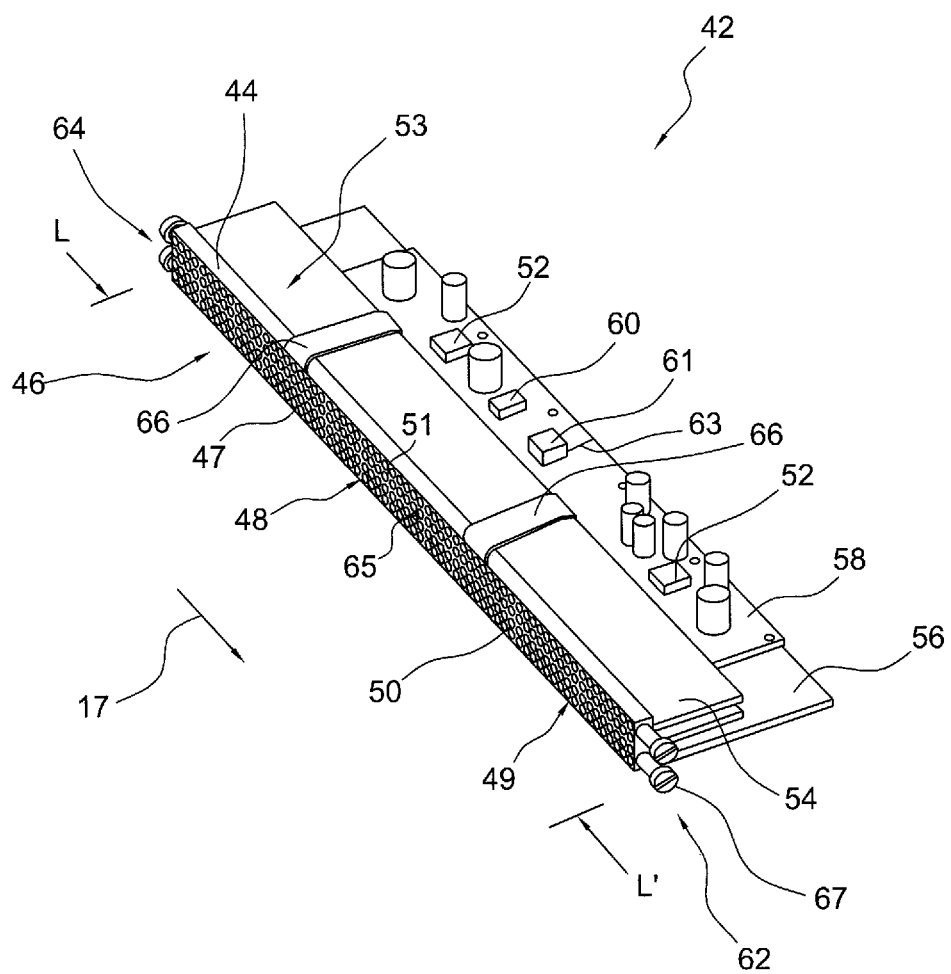
FIG. 4 shows a perspective view of a light module which can be used in the apparatus of FIG. 1; and, FIG. 5 is a schematic showing the light sources arranged in four columns on a light module.

A plurality of light modules 42 are arranged between the diffusing screen 34 and the longitudinal carriers 16. As shown in FIG. 4, each light module 42 has a rigid and self-supporting metallic carrier body 44 having a front side 46. A plurality of light sources 48 are arranged on the front side 46. In the preferred embodiment, the light sources 48 are arranged on a flexible carrier foil 47, as it is usually used in the realization of flexible conducting paths, for instance, for the electrical connection of foldable notebook displays. The carrier foil 47, here, is directly bonded on the front side 46 of the carrier body 44 with heat-transferring adhesives. Thus, the light sources only get their defined alignment through the rigid carrier body.

In preferred embodiments, the entire front side 46 of every light module 42 is evenly covered with light sources 48 which have the same lateral distances to each other. The light sources 48 are arranged in a matrix which includes four columns in the longitudinal direction 17 and sixty-four rows transverse thereto.

Figure 5:
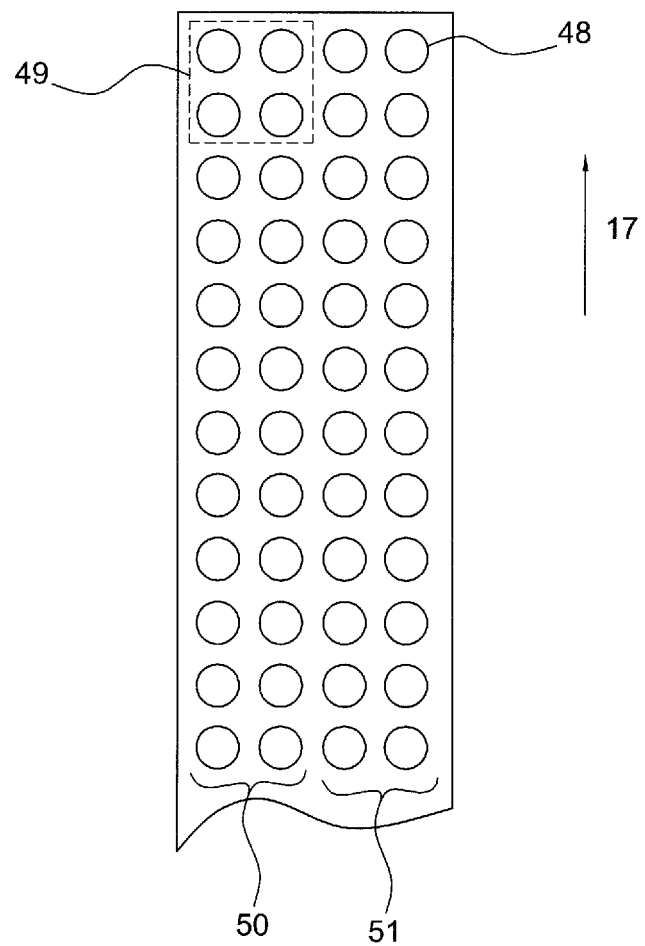

FIG. 5 shows a portion of a matrix and the four columns (50, 51) of light sources 48. In the embodiment preferred at this time, the light sources 48 are white LEDs which are fixed on the carrier foil 47. Four LEDs which form the corner points of a square, are each combined to a 4-tuple 49 as shown in FIG. 5. The LEDs 48 in each 4-tuple 49 are connected in series and are thus only controllable as a group, so that they function as a virtual light source having four times the light intensity. The series connection is preferred over a parallel connection which is also possible, because all LEDs of a 4-tuple 49 have the same current flow through them and thus glow with the same brightness. The 4-tuples 49 are arranged in two parallel rows (50, 51) in the manner shown in FIG. 5. The two parallel rows extend over the length L-L' of the light modules 42. Within the two rows (50, 51), each 4-tuple 49 can be individually controlled. Also, the 4-tuples of different rows (50, 51) can be separately controlled. Advantageously, the LEDs 48 not only can be turned on and off but also have their brightness changed from 0% to 100%.

In the preferred embodiments, each light module has two separate voltage supplies 52. The 4-tuples 49 of each row (50, 51) are alternately connected to one or the other voltage supply so that two adjacent 4-tuples 49 are each connected to different voltage supplies. In other words, the 4-tuples 49 of the two rows (50, 51) are connected in two opposing "zig-zag" rows. This is advantageous for generating chessboard-like light-dark patterns which are especially suited for particular surface inspections.

On the back side 53 of the carrier body 44, a number of cooling fins (54, 56) are farmed which, here, extend over the entire length L-L' of the light modules 42. In the shown embodiment, each light module 42 has three cooling fins. A (lower) outer cooling fin 56 has a larger surface than the two adjacent cooling fins 54. The cooling rib 56 projects beyond the cooling ribs 54 radially outwardly to the rear.

On the cooling fin 56 there is arranged a conventional circuit board 58, advantageously on a thermally conductive paste. The circuit board 58 carries control electronics for the light sources 48. The control electronics include, amongst other things, the two separate voltage sources 52 as well as a microprocessor 60 with an associated memory 61. The memory 61, here, includes a non-volatile memory in which, inter alia, a plurality of pattern fragments can be pre-defined and stored. The pattern fragments of all light modules 42 complement each other to a defined overall pattern which can be generated with the help of the light sources 48 on the diffusing screen 34. In other words, the pattern fragments in the memories 61 represent the control information which each individual light module requires in order to control each of the light sources 48 so that a defined overall pattern results on the diffusing screen 34. Advantageously, each light module 42 has a bus connection via which the pattern fragments can be loaded into the memory 61. Further, it is advantageous if each light module has an additional, separate control line 63 which is configured to generate a trigger signal for sequential switching the different pattern fragments in the memory 61. The provision of a separate control line 63 enables a uniform, synchronous "hardware trigger" for simultaneous switching of the pattern fragments of all light modules 42, a fact which is advantageous to switch between patterns very fast. Advantageously, the control lines 63 of all light modules 42 are electrically connected with each other.

Further, it is advantageous when individually calibrated data for each light module are stored in the non-volatile memory. With the aid of such calibration data, the radiation intensity of all light modules 42 can very easily be adapted to each other, which contributes to a very even pattern. Preferably, at least one temperature sensor 65 is arranged between the light sources 48 on the front side 46 of the carrier foil 47. The temperature sensor 65 serves to avoid a thermal overload of the light modules. Furthermore, it is advantageously used for an online-calibration of the light modules 42.

The carrier foil 47 has two integral straps 66 which are guided over the upper cooling fin 54 to the circuit board 58. The integral straps 66 include conducting paths (not shown here for the sake of clarity) with which the light sources 48 are connected to the control electronics.

Each light module 42 has a top end 62 and a bottom end 64. Threaded pins 67 are arranged on each end (62, 64) with the aid of which the light modules 42 can be fixed on the transverse carriers (12, 14). FIG. 3, in an enlarged view, shows how the light modules 42 are mounted with the aid of the threaded pins 67 in the preferred embodiment. In the preferred embodiment, the light modules 42 are floatingly mounted on the transverse carriers (12, 14) in the longitudinal direction 17, that is, the light modules can expand or contract in the longitudinal direction 17 without mechanical tension occurring in the apparatus 10. Advantageously, this is achieved in the longitudinal direction 17 by a fixed support and a floating support.

As shown in FIG. 3, the cooling fins (54, 56) form cooling channels which run in parallel to the longitudinal direction 17 and expand radially from the inside to the outside. The cooling channels are covered radially on the outside by the enclosure 26 which, with the aid of the fan 24, generates a defined air flow through the openings (18, 20, 22). In a preferred embodiment, cooling air outlets 68 are arranged in the transverse carriers (12, 14). The cooling air outlets 68 are advantageously arranged directly above the cooling fins (54, 56).

As shown in FIG. 3, a number of holding clamps 70 are arranged on the transverse carriers. In the present case, the holding clamps 70 are distributed around the circular segment-shaped cutout 32. Here, the holding clamps 70 are U-shaped elements which are configured to exchangeably fix the diffusing screen 34. In the embodiment shown here, the diffusing screen 34 can be tangentially inserted into the holding clamps 70 from the lateral opening of the inspection space 36. In the preferred embodiment, the diffusing screen is a bendable plastic plate of acrylic glass. In another embodiment, the diffusing screen is made of a full-volume translucent but non-transparent PTFE-material. However, it can also be a different, preferably milkglass-like plastic plate. The plastic plate is brought into the circular shape of the cutout 32 by the insertion into the holding clamps 70. The inner material tension of the plastic plate presses the diffusing screen 34 radially outwardly so that the diffusing screen 34 is held in a radially fixed position with the aid of the transverse carriers (12, 14) and the holding clamps 70. The diffusing screen 34 can expand or contract tangentially. Further, the holding clamps 70 provide a certain play in the longitudinal direction 17, so that the diffusing screen 34 is also floatingly mounted in the longitudinal direction in this embodiment.

A transverse beam on which a camera 74 is arranged is identified by the reference character 72 in FIG. 3. A further camera 74' is arranged on a further beam 76. The cameras (74, 74') are area scan cameras in a preferred embodiment, that is, cameras with an area-type image sensor having a plurality of pixels arranged matrix-like. In a preferred embodiment, the apparatus 10 also has a further camera 78 shown in FIG. 1 which is arranged in a housing on the back side of the apparatus 10. In a preferred embodiment, the camera 78 is a line-scan camera with a line-shaped image sensor. The optical axis 80 of the line-scan camera 78 is exactly perpendicular to the longitudinal center axis 40. The optical axis 80 of the camera 74' runs transversely but not necessarily exactly in parallel to the longitudinal center axis 40 of the apparatus 10. In comparison thereto, the camera 74 looks from the outside and into the tunnel-shaped inspection space 36 nearly in parallel to the longitudinal center axis 40. The cameras (74, 74') can advantageously be pivoted so that the viewing direction into the inspection space 36 can be varied.

As is further shown in FIG. 3, the transverse beam 72 is fixed on the transverse carrier 12 outside of the inspection space 36. In the embodiment shown here, the transverse carrier 12 has a predefined mounting position for the transverse beam 72 and the camera 74 can be shifted along the transverse beam 72. The predefined, indexed mounting positions for the transverse beam 72 enable a simple mounting and dismounting of the camera 74, for example, to exchange the diffusing screen 34 or for other reasons. Because of the indexed mounting positions, the camera 74 can be quickly brought back to its original position. It is also conceivable that the position and viewing direction of the cameras (74, 74') can be varied with the aid of a robot on which the cameras (74, 74') are mounted.

The reference character 82 in FIG. 3 references a closing plate which, in the preferred embodiments, can be fixed in the cutout 32 of the transverse carrier 12 in order to close the tunnel-shaped inspection space 36 toward the top. A corresponding closing plate 82 can be mounted at the bottom end of the inspection space 36. In one embodiment, the closing plate 82 is formed at the bottom end of the inspection space 36 by a workpiece receptacle on which the object to be inspected is placed. The workpiece receptacle (not shown more closely here) can advantageously be arranged on a lift 84 shown in FIG. 1 with which the object to be inspected can be transported into the inspection space 36 from below.

The closing plate 82 at the top end of the inspection space 36 has an opening 86 through which the camera 74 can look into the inspection space 36 when the closing plate 82 is fixed on the transverse carrier 12. In preferred embodiments, the inner side 88 of the closing plate 82 is reflective or provided with light sources 48 (not shown here).

As shown in FIG. 1 the apparatus 10 is configured to generate a light-dark pattern 90 on the diffusing screen 34 with the aid of the light sources 48. For reasons of clarity, the pattern 90 is only partially indicated in FIG. 1. An evaluation and control unit which controls the light sources 48 and the cameras (74, 78) is shown in FIG. 1 with the reference character 92. It is understood that the evaluation and control unit 92 can also be realized separately from the mechanical arrangement with the transverse carriers (12, 14) and the longitudinal carriers 16. In particular, a personal computer with appropriate interfacing hardware can be used as the evaluation and control unit 92 for controlling the light sources 48 and the cameras (74, 78) and where appropriate, for controlling the lift 84.

In a preferred embodiment, the evaluation and control unit is configured to generate a light-dark pattern 90 with a sinusoidal brightness gradient on the diffusing screen 34 with the aid of the light sources 48. Further, the evaluation and control unit 92 is configured to shift the light-dark pattern 90 with the sinusoidal brightness gradient relative to the surface to be inspected. This can be effected via an appropriate controlling of the light sources 48 either electronically and/or through a mechanical movement of the object to be inspected. The latter can be advantageously realized with the aid of a workpiece receptacle which is rotatable about the longitudinal axis 40 (not shown in detail here).

In the preferred embodiments, the light-dark pattern 90 includes stripes which are shifted transversely to the stripe direction. The evaluation and control unit 92 is configured to evaluate a plurality of images of the surface to be inspected with the (relative thereto) shifted stripe patterns 90. Through the phase reconstruction on the basis of the images, the local inclinations of the surface to be inspected can be determined. A particularly preferred method for evaluating the images is described in the German patent application DE 10 2007 063 530.5 which is fully incorporated herein by reference. Further, it is advantageous when the evaluation and control unit 92 is configured to generate a plurality of overlaid stripe patterns simultaneously, as described in international application WO2009/007130 which is also fully incorporated herein by reference.

As can be seen from FIGS. 1 to 3, the transverse carriers (12, 14) in the shown embodiments are mounted largely identically but are mirrored to one another on a frame 94. The frame 94 enables a simple loading of the inspection space 36 from below with the aid of the lift 84. In a preferred embodiment, the lift 84 is connected to a conveyor belt (not shown here) via which objects to be inspected are automatically supplied. Principally, it is conceivable to configure the apparatus 10 such that an individual diffusing screen 34 is manually or automatically inserted into the cutout 32 for every object to be inspected or for every type of object to be inspected. Thereby, the light-dark patterns 90 can be printed on the diffusing screen 34 or otherwise be permanently applied thereto. The light-dark patterns 90 are "activated" by an even illumination with the aid of the light sources 48.

Further, it is conceivable that the light sources 48 are realized using organic LEDs, so called OLEDs. Further, mirrors can be arranged within the inspection space 36 and/or on the base in order to make, for example, undercuts on the objects to be inspected visible to the cameras (74, 78).

It is understood that the foregoing description is that of the preferred embodiments of the invention and that various changes and modifications may be made thereto without departing from the spirit and scope of the invention as defined in the appended claims.

What is claimed is:

1. An apparatus for optically inspecting an at least partially reflecting surface of an object, the apparatus comprising:
   first and second transverse carriers defining respective substantially circular segment-shaped cutouts;
   said first and second transverse carriers being arranged at a longitudinal distance (D) from each other and said longitudinal distance defining a longitudinal direction;
   a plurality of longitudinal members configured to hold said first and second transverse carriers at said longitudinal distance (D);
   said longitudinal members being arranged at a defined radial distance to said circular segment-shaped cutouts;
   a translucent diffusing screen which is held in said circular segment-shaped cutouts by said transverse carriers to form a tunnel-shaped inspection space;
   a multiplicity of light sources arranged outside of said tunnel-shaped inspection space between said longitudinal members and said diffusing screen;
   said light sources being configured to be controlled individually or in small groups to generate variable light-dark patterns on said diffusing screen;
   wherein said longitudinal members and said diffusing screen form a substantially closed enclosure for providing a cooling air flow past said light sources;
   a workpiece receptacle configured for accommodating the object in said tunnel-shaped inspection space;
   at least one camera which is directed into the tunnel-shaped inspection space; and,
   an evaluation and control unit configured to control said light sources and said camera to generate different ones of said light-dark patterns on said diffusing screen and to record and evaluate a plurality of images of said object in dependence on said light-dark patterns.

2. The apparatus of claim 1, further comprising:
   a plurality of identical light modules arranged between said diffusing screen and said longitudinal members; and,
   each of said light modules including a plurality of said multiplicity of light sources.

3. The apparatus of claim 2, wherein:
   said light modules each have a metallic carrier body having a length (L-L') which is approximately equal to said longitudinal distance (D); and,
   said carrier body has a front side on which said plurality of light modules are arranged and a back side on which cooling ribs are formed.

4. The apparatus of claim 2, wherein said light modules are floatingly mounted on said transverse carriers.

5. The apparatus of claim 2, wherein:
   each of said light modules has two pairs of columns of light sources which are parallel in the longitudinal direction; and,
   said pairs of columns are configured to be individually controlled.

6. The apparatus of claim 1, wherein said light sources are each mounted at the same radial distance to said diffusing screen.

7. The apparatus of claim 1, wherein said diffusing screen comprises a diffusively scattering ground material.

8. The apparatus of claim 1, wherein said diffusing screen is floatingly mounted on said transverse carriers.

9. The apparatus of claim 1, wherein said transverse carriers have holding clamps configured to exchangeably fix said diffusing screen.

10. The apparatus of claim 1, further comprising a plurality of fans arranged on said longitudinal members.

11. The apparatus of claim 1, wherein said substantially closed enclosure is arranged approximately concentrically to said diffusing screen.

12. The apparatus of claim 1, wherein said transverse carriers are arranged vertically above one another.

13. The apparatus of claim 1, further comprising:
   a transverse beam arranged in said longitudinal direction and mounted outside of said tunnel-shaped inspection space; and,
   at least one camera mounted on said transverse beam.

14. The apparatus of claim 1, wherein said camera defines an optical axis which is arranged substantially perpendicular to said longitudinal direction.

15. The apparatus of claim 1, further comprising:
   a closure plate configured to close said tunnel-shaped inspection space in said longitudinal direction; and,
   said closing plate having an inner side facing toward said inspection space and being configured to generate a further pattern with light and dark regions.

16. The apparatus of claim 7, wherein said diffusively scattering ground material is selected from the group consisting of an acrylic glass and a full-volume polytetrafluoroethylene (PTFE) material.

\* \* \* \* \*

UNITED STATES PATENT AND TRADEMARK OFFICE
CERTIFICATE OF CORRECTION

| | | |
|---|---|---|
| PATENT NO. | : 8,605,146 B2 | Page 1 of 1 |
| APPLICATION NO. | : 13/171105 | |
| DATED | : December 10, 2013 | |
| INVENTOR(S) | : K. Knupfer et al. | |

It is certified that error appears in the above-identified patent and that said Letters Patent is hereby corrected as shown below:

In the Specification

<u>In Column 6</u>:
Line 11: delete "configuration:" and substitute -- configuration. -- therefor.

<u>In Column 10</u>:
Line 58: delete "farmed" and substitute -- formed -- therefor.

Signed and Sealed this
Fifteenth Day of April, 2014

Michelle K. Lee
*Deputy Director of the United States Patent and Trademark Office*